US00PP29928P3

(12) United States Plant Patent
Olesen

(10) Patent No.: US PP29,928 P3
(45) Date of Patent: Dec. 4, 2018

(54) MINIATURE ROSE PLANT NAMED 'POULPAR095'

(50) Latin Name: ***Rosa* hybrid**
Varietal Denomination: Poulpar095

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 52 days.

(21) Appl. No.: 15/330,305

(22) Filed: Sep. 6, 2016

(65) Prior Publication Data

US 2018/0070493 P1 Mar. 8, 2018

(51) Int. Cl.
*A01H 5/02* (2018.01)
*A01H 6/74* (2018.01)

(52) U.S. Cl.
USPC ..... Plt./116
CPC ..... *A01H 5/02* (2013.01); *A01H 6/749* (2018.05)

(58) Field of Classification Search
USPC ..... Plt./116
See application file for complete search history.

(56) References Cited

PUBLICATIONS

Perfection by Poulsen, Oct. 2013.*

* cited by examiner

*Primary Examiner* — Keith O. Robinson

(57) ABSTRACT

A new garden rose plant of the Miniature class which has abundant, red purple flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar095'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar095', originated as a single seedling from the stated cross.

The new variety may be distinguished from its male pollen parent and female seed parent primarily by the following characteristics. The male pollen parent plant has apricot blend flowers, while the new variety has red purple flowers. The female seed parent plant has orange blend flowers, while the new variety has red purple flowers.

The objective of the hybridization of this rose variety was to create a new and distinct variety for garden use with unique qualities, such as:

1. Uniform and abundant red purple flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar095' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar095' was selected in the spring of 2008 by the inventor as a single plant from the progeny of the aforementioned hybridization.

Asexual reproduction of 'Poulpar095' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpar095' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar095'.

Specifically illustrated in FIG. 1 are open flowers viewed from above and the side, flower petals detached, reproductive flower parts, and flower buds at various stages of opening.

Figure 1:
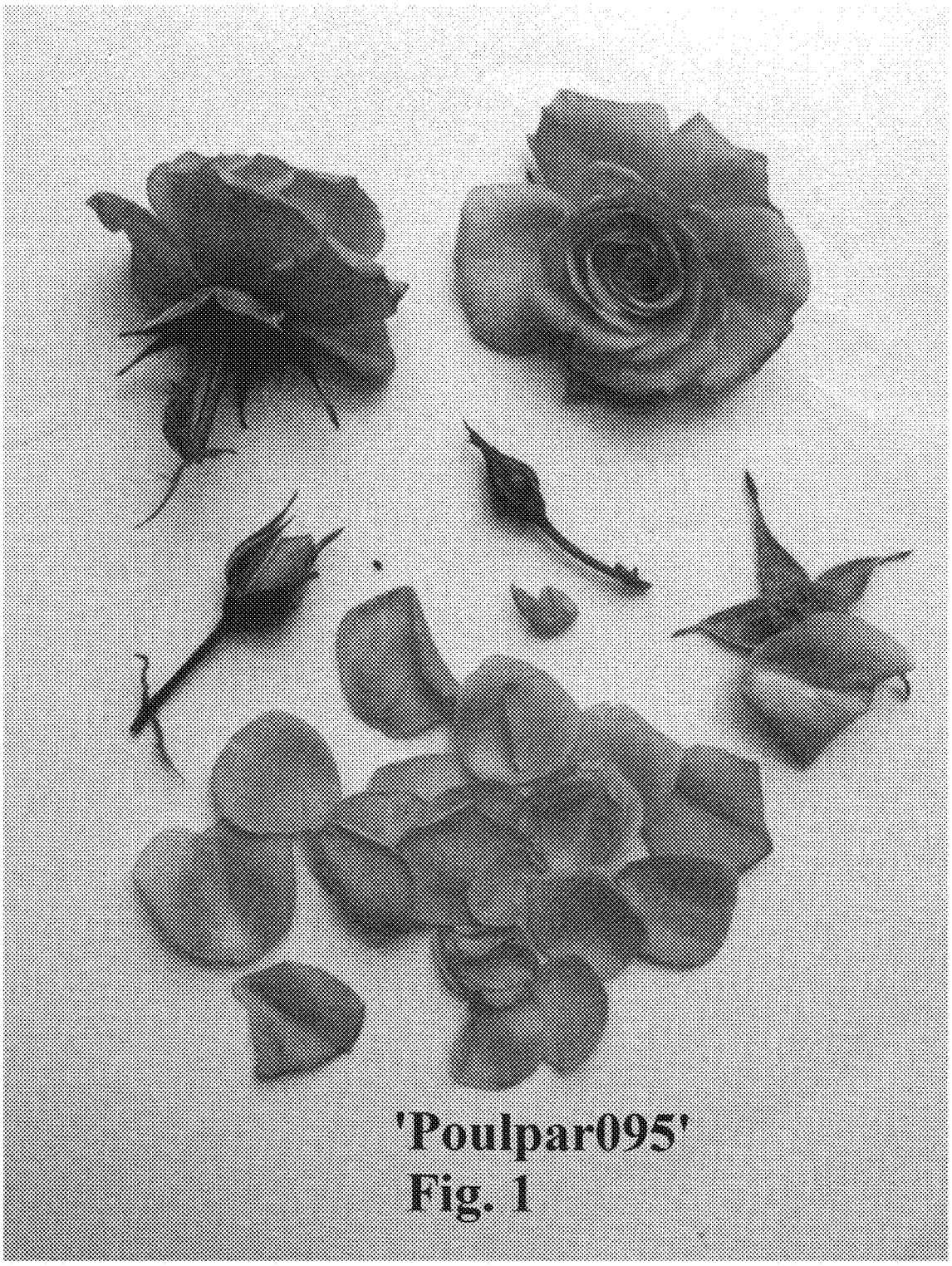
Figure 2:
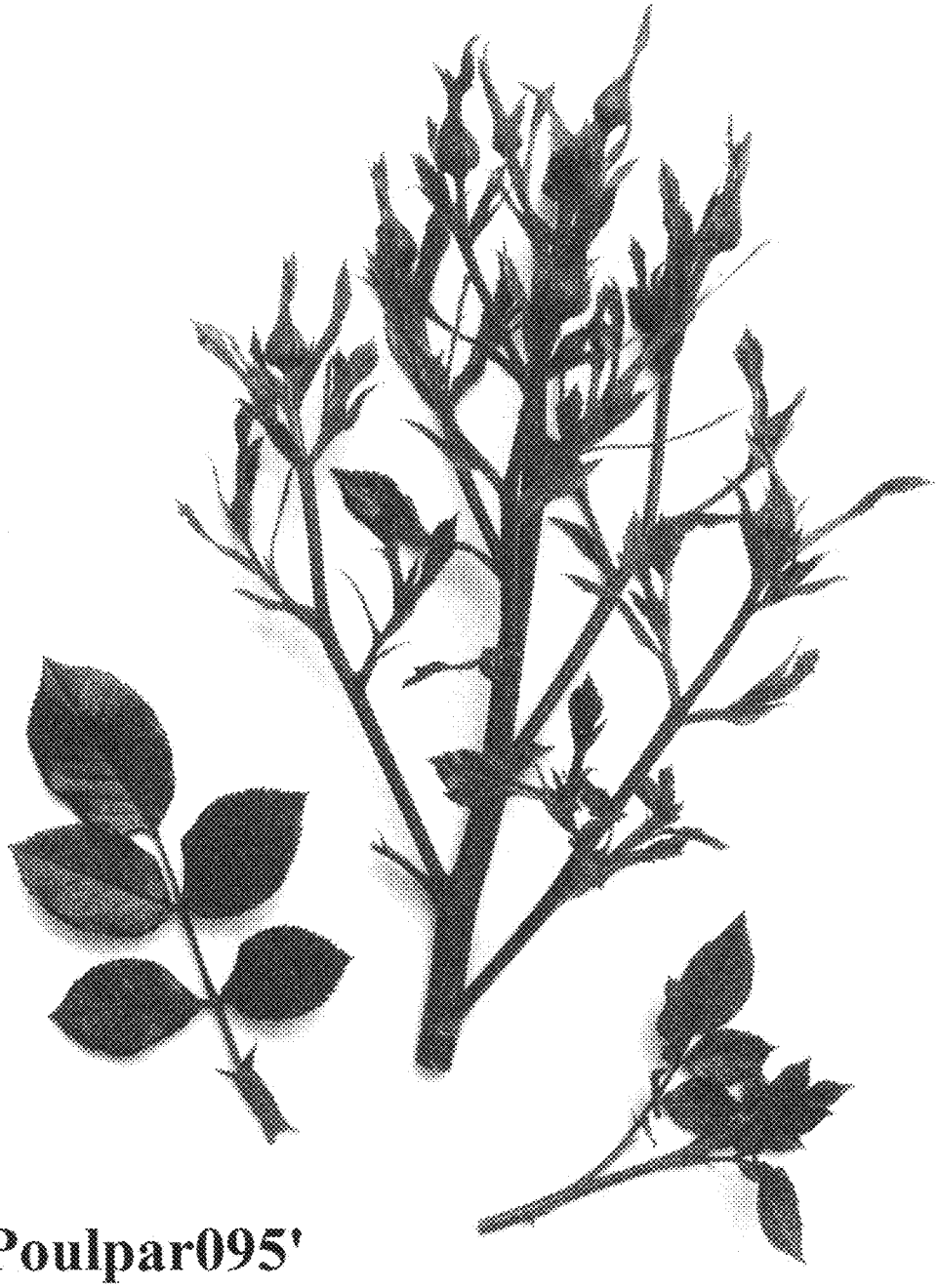

Illustrated in FIG. 2 are mature and juvenile leaves, and a bare stem showing attachment of peduncles, pedicels and flower buds. Plants shown are 2 years of age.

DETAILED DESCRIPTION OF THE VARIETY

The following is a description of 'Poulpar095', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poultipe', U.S. Plant patent application Ser. No. 09/287,291 filed Mar. 31, 1999 now abandoned, are compared to 'Poulpar095' in Chart 1.

CHART 1

| | 'Poulpar095' | 'Poultipe' |
|---|---|---|
| Petal Count | 35 | 30 |
| Flower Diameter | 50 mm | 30 mm |
| General Tonality of Flower Color | Red Group 55A and Red Group 38A | Red-Purple Group 62A |

FLOWER AND FLOWER BUD

Blooming habit: Continuous.

Flower bud:

*Size*.—Upon opening, 14 mm in length from base of receptacle to end of bud. Bud diameter is 10 mm.

*Bud form*.—Broad based ovoid.

*Sepal inner surface*.—Color: Yellow-Green Group 145C. Surface: Lightly pubescent.

*Sepal outer surface*.—Color: Yellow-Green Group 144A with intonations of Greyed-Purple Group 183A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—20 mm long, 7 mm wide.

*Receptacle*.—Texture: Smooth. Size: 3 mm in height, 4 mm wide. Color: Yellow-Green Group 144A. Shape: Campanulate.

*Pedicel*.—Surface: Small prickles. Length: 20 mm. Diameter: 2 mm on average. Color: Yellow-Green Group 144A with intonations of Greyed-Red Group 181A. Strength: Average.

*Peduncle*.—Length: 2 to 9 cm. Diameter: About 4 mm. Color: Yellow-Green Group 145A with intonations of Greyed-Red Group 181A. Texture: Smooth.

Flower bud development: Flower buds are borne in corymbs of about 3 flower buds on each peduncle.

Flower bloom:

*Flower type*.—Double.

*Fragrance*.—Moderate rose perfume.

*Duration*.—The blooms have a duration on the plant of approximately 7 to 10 days. Petals fall cleanly away from plant after flowers have fully matured.

*Size*.—Flower diameter is 50 mm when open. Flower depth is 20 mm.

*Flower shape*.—High centered with a high pointed center which is tightly closed.

*Shape of flower, side view*.—The upper portion is flattened convex. The lower portion is flat.

Petalage: Under normal conditions, flowers have about 35 petals.

General tonality of flower: Open flowers are Red Group 55A and Red Group 38A.

Petal color:

*Outer and inner petals*.—Upper surface: Red Group 52D splashed with Red Group 52B with a basal petal spot of Yellow Group 7B. Petal spots are about 5 mm in height and 5 mm wide on the upper surface. Lower surface: Red Group 52C splashed with intonations of Red Group 50B with a basal petal spot of Yellow Group 7B. Petal spots are about 4 mm in height and 4 mm wide on the under surface.

Petals:

*Petal reflex*.—Moderate reflex.

*Margin*.—Entire and uniform

*Shape*.—Broad ellipse. Apex shape: Rounded. Base shape: Acute.

*Size*.—Up to 23 mm (l)×23 mm (w).

*Texture*.—Smooth.

*Thickness*.—Average.

Petaloids:

*Size*.—10 mm (l) by 5 mm (w).

*Quantity*.—About 5.

*Shape*.—Apex and base are acute.

*Color*.—Red Group 52D on the upper surface and Red Group 52C on the lower surface.

Reproductive flower parts:

*Pollen*.—None observed.

*Anthers*.—Size: 1 mm in length. Color: Yellow Group 11C. Quantity: 40 on average.

*Filaments*.—Color: Yellow Group 9A. Length: 3 mm.

*Pistils*.—Length: 4 mm. Quantity: 20 on average.

*Stigmas*.—Color: White Group 155A.

*Styles*.—Color: White Group 155A.

*Location of stigmas*.—Level in location relative to the length of the filaments and the height of the anthers.

*Hips*.—None Observed.

PLANT

Plant growth: Upright, bushy. Plants are 30 cm in height, and 30 cm wide.

Stems:

*Color*.—Juvenile growth: Yellow-Green Group 146B with intonations of Greyed-Purple Group 183C. Mature growth: Yellow-Green Group 146B with intonations of Greyed-Purple Group 183C.

*Length*.—On average, canes are 15 cm from the base of the plant to the flowering portion.

*Diameter*.—8 mm.

*Internodes*.—On mature canes about 22 mm between nodes.

*Surface texture*.—Young wood: Smooth. Older wood: Smooth.

Long prickles:

*Incidence*.—None observed.

Plant foliage:

*Compound leaf*.—100 mm (l)×50 (w).

*Quantity*.—About 3 leaves per 10 cm of stem on average.

*Leaf bearing angle to the stem*.—45 degrees.

*Color of juvenile foliage*.—Upper side: Greyed-Purple Group 183A and Yellow-Green Group. Lower side: Greyed-Purple Group 183A and Yellow-Green Group.

*Color of mature foliage*.—Upper side: Yellow-Green Group 146A. Lower side: Yellow-Green Group 147C.

Plant leaves and leaflets:

*Stipules*.—Size: 18 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 2 mm.

*Upper surface*.—Color: Yellow-Green Group 144A with intonations of Greyed-Purple Group 183A.

*Lower surface*.—Color: Yellow-Green Group 144A.

*Rachis*.—Length: 30 mm Upper surface: Color: Yellow-Green Group 144A with intonations of Greyed-Purple Group 183A.

*Lower surface*.—Color: Yellow-Green Group 144A.

*Leaflet*.—Quantity: Normally 5 leaflets. Margins: Serrated. Size: On average terminal leaflets are 35 mm long, 25 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Miniature rose class named 'Poulpar095', substantially as illustrated and described herein, due to its abundant red purple flowers, disease resistance, and extended period of bloom.

* * * * *

'Poulpar095'

'Poulpar095'